(12) United States Patent
Nilsson

(10) Patent No.: US 6,471,516 B1
(45) Date of Patent: Oct. 29, 2002

(54) MEANS FOR INSERTING FILLING MATERIAL DURING DENTAL TREATMENT

(75) Inventor: John Thorleif Nilsson, Finnsnes (NO)

(73) Assignee: Dental Innova AS, Finnsnes (NO)

( * ) Notice: Subject to any disclaimer, the term of this patent is extended or adjusted under 35 U.S.C. 154(b) by 0 days.

(21) Appl. No.: 09/380,776
(22) PCT Filed: Mar. 12, 1998
(86) PCT No.: PCT/NO98/00082
§ 371 (c)(1), (2), (4) Date: Dec. 1, 2000
(87) PCT Pub. No.: WO98/41166
PCT Pub. Date: Sep. 24, 1998

(30) Foreign Application Priority Data

Mar. 14, 1997 (NO) ................................................ 971195

(51) Int. Cl.$^7$ .................................................. A61C 3/08
(52) U.S. Cl. ........................................................ 433/164
(58) Field of Search ............................ 433/164, 29, 39, 433/226

(56) References Cited

U.S. PATENT DOCUMENTS

| | | | | |
|---|---|---|---|---|
| 1,252,179 A | * | 1/1918 | Risley | 433/164 |
| 4,586,901 A | * | 5/1986 | Tanaka et al. | 433/164 |
| 5,030,093 A | * | 7/1991 | Mitnick | 433/164 |
| 5,759,032 A | * | 6/1998 | Bartel | 433/29 |
| 5,791,898 A | * | 8/1998 | Maissami | 433/164 |

* cited by examiner

Primary Examiner—Nicholas D. Lucchesi
(74) Attorney, Agent, or Firm—Quarles & Brady LLP

(57) ABSTRACT

A compactor for placing light-curable filling material in connection with dental treatment, especially for filling a cavity in a tooth which is contiguous with an adjacent tooth, the compactor in the longitudinal direction having a tapering, conical shape; the end which is to be pressed down in the filling has in cross section a square, rounded shape; one of the longitudinal side faces is concave in form, whilst the opposite side face is convex in form, and in the end which is furthest from the filling, the compactor is equipped with an opening and hole for connection to a handle, e.g., an amalgam plugger.

5 Claims, 2 Drawing Sheets

Figure 1:
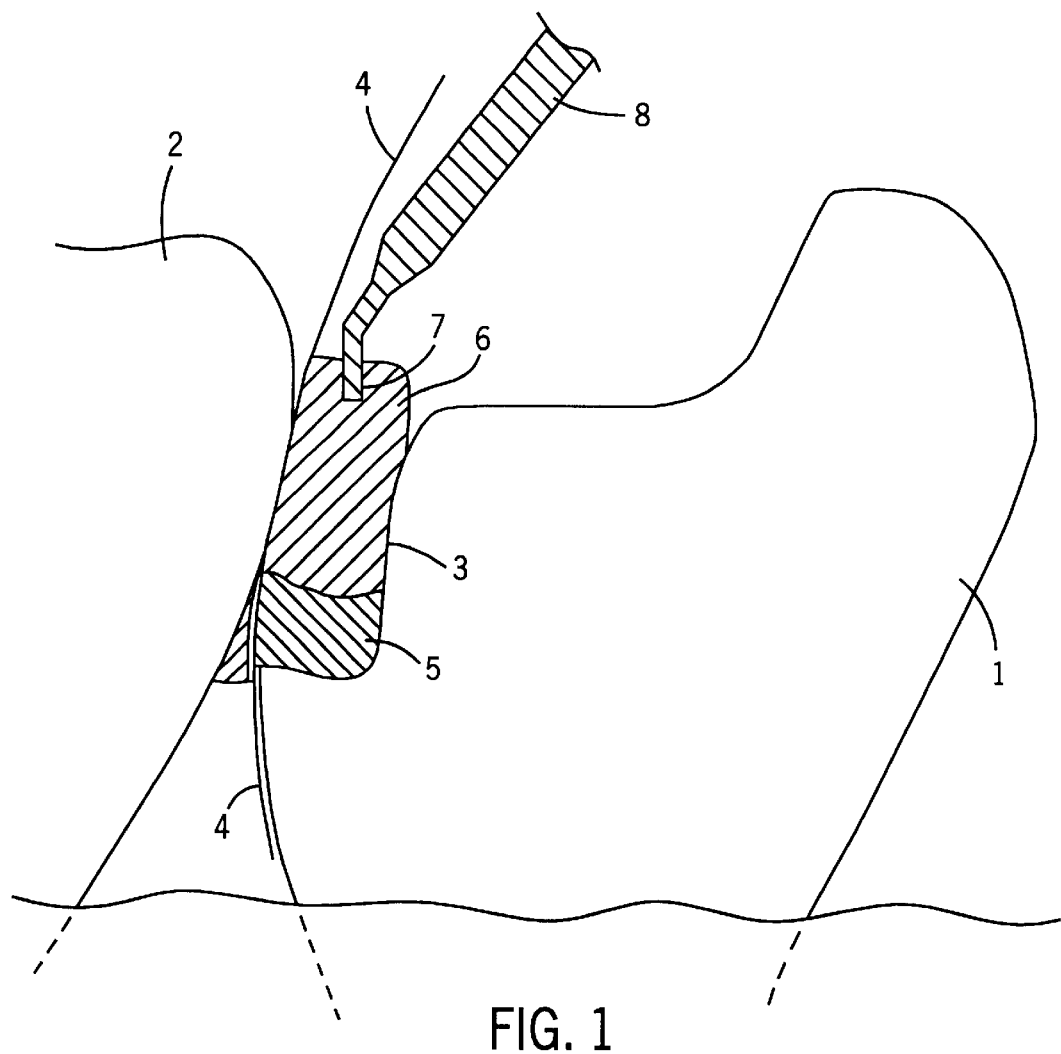

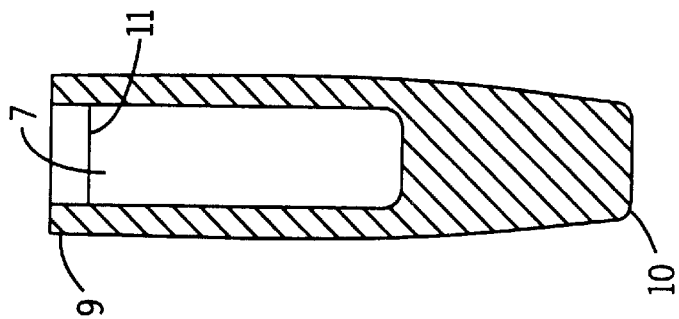
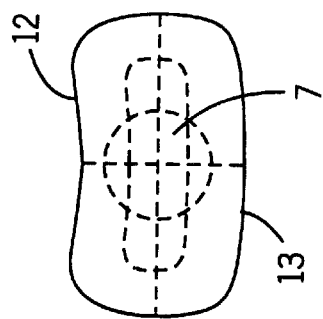
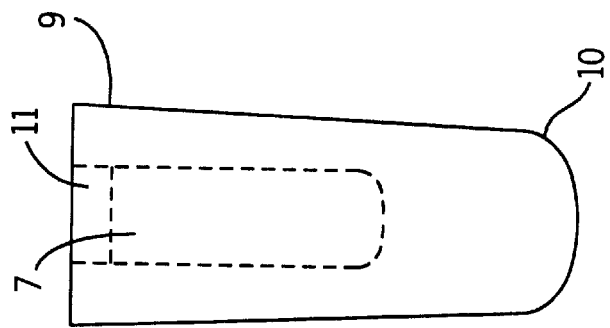

MEANS FOR INSERTING FILLING MATERIAL DURING DENTAL TREATMENT

The invention relates to a device for the mechanical compaction of filling materials in cavities (holes) in teeth. To be more precise, the invention relates to a compactor which is used to press light-curable plastic fillings, glass ionomers and chemically curable materials in place in a cavity.

Today's methods and tools for plastic fillings of so-called Class II fillings (i.e., in the back teeth) do not give a satisfactory result with respect to compactness and thus strength in the fillings. For this reason, it is today a widespread problem that fillings of this kind have an unduly short life, that is to say that they fall out wholly or in part a short time after the filling has been placed. This means that the dentists receive complaints from their patients and must put in new fillings. The object of the compactor according to the invention is to eliminate or at least significantly reduce this problem.

Today. plastic fillings account for 60% of all fillings and they are gradually replacing the less popular amalgam fillings. Amalgam fillings have acquired an ever-poorer reputation because of the possible effects they may have on a person's health owing to their high mercury content.

The instrument that dentists use today is adapted to conventional amalgam fillings, and is not designed for modern filling materials such as plastic fillings, glass ionomers and composites.

The closest instrument found today that is comparable with the compactor of the invention is the so-called "light-tip" which is produced in Sweden. This product is in fact transparent, but is made of a hard material and it is the intention that the tip should be mounted on the end of the curing lamp. However, its shape is entirely different from that of the compactor according to the application. It only makes points of contact with the adjacent tooth. For these reasons, the same pressure is not obtained with this product and nor is the contraction which occurs when the tip is withdrawn after curing avoided.

U.S. Pat. No. 5,030,093 describes a method and apparatus for placing, compacting and shaping a light-curable tooth filling material. It describes a combination apparatus which ensures that the filling material is hardened by means of light.

SE 435 447 describes a method and device for making a light-curable tooth filling. A conical adapter is mounted on the end of a light means, and this is supposed to facilitate the curing of the filling material in the deeper parts of a cavity.

The object of the present compactor is to provide a device where mechanical compaction of the filling material can be carried out before and during curing.

This is accomplished in that to obtain mechanical effect on a tooth filling in a cavity during placement, use is made of the compactor wherein there is an opening for partially movable connection thereof to an instrument for the transmission of said mechanical effect, the compactor being made of a transparent and partly elastic material.

Further details of the invention are set forth in the following description and drawings, wherein:

FIG. 1 shows a hole (cavity) which has been drilled in a tooth, where the cavity faces an adjacent tooth.

FIG. 2*a* shows the flexible compactor seen from in front;

FIG. 2*b* shows the flexible compactor seen from above; and

FIG. 2*c* shows the flexible compactor seen from the side.

FIG. 1 shows a tooth 1 with a drilled cavity 3 next to an adjacent tooth 2. In order to place composites or light-curable glass ionomers, hereinafter referred to as filling materials, in premolars or molars and incisors (i.e., Class I, II and III fillings) which face the adjacent tooth 2, there are some problems that must be solved in order to obtain a properly functioning filling. After a cavity 3 has been drilled in the tooth 1 where the cavity faces towards an adjacent tooth or adjacent teeth, a matrix strip 4 of plastic or metal having a wedge is put in place. The cavity 3 is lined and the bonding agent applied, i.e., put on. Bonding agent is an adhesive which is applied in order to create a strong attachment between tooth and filling material. The filling material 5 is pressed down and condensed as best as can be in the cavity 3. It is with this filling that the compactor 6 according to the invention comes into its own. Owing to an optimal shape, a much better pressure is obtained both down against the tooth 1 and against the side of the adjacent tooth 2. Thus, a much more compact filling is obtained. The filling is cured by means of a curing lamp which is aligned as closely as possible with the compactor. Since the compactor 6 is transparent, the light passes therethrough and cures the composite 5 until this becomes hard. Normal curing time is about 30 to 40 seconds. Then, the process is continued, placing layer upon layer of filling material 5 and the whole filling will ultimately consist of 3 to 4 such layers.

As regards curing lamps, there are various types having different properties. The curing of the filling material 5 takes place at a specific temperature and wave length. The curing takes place in that the curing lamp, which emits long-wave blue light, is held against the filling material for about 40 seconds.

As can be seen from FIG. 2. the compactor 6 is wider at the top 9 that at the bottom 10, and this shape makes it more suited to releasing the filling material. The rounded lower shape 10 ensures optimal pressure against the filling material during compaction.

The compactor is designed to be wider at the top 9 than at the bottom 10 (FIG. 2*a*) so that it will more easily release the cured filling material 5 after curing has been completed. In addition, it has a hole 7 in the centre so that a standard "filling plugger" amalgam plugger (handle) 8 in plastic or steel can be used, i.e., the compactor 6 is mounted on the end of this plugger 8. The hole 7 inside the compactor must be larger than the opening 11, since the compactor must be capable of being turned 360° relative to the amalgam plugger. Seen from above (FIG. 2*b*), the compactor will curve slightly inwards 12 on one of the long sides, and slightly outwards 13 on the other long side. This will be optimal relative to the shape of the cavities and the teeth against which the compactor is to be pressed. In the end 10, the compactor will have a face with slightly curved edges so that an optimum pressure face is obtained down against the tooth and out against the sides of the tooth.

One of the most essential aspects of the compactor 6 is that it has a shape which ensures optimal pressure, and also that it ensures a flexibility in the possibility of applying pressure both down on the tooth and in towards the side of the tooth. This can be illustrated thus:

First the compactor is pressed down against the cavity in the tooth so that the inserted filling material 5, i.e., the material placed obliquely down on both sides of the tooth, is attached to the bottom of the tooth. Subsequently downward pressure is applied on the side of the tooth thereby ensuring that the composite 5 is attached to the adjacent tooth. Owing to the unique shape of the compactor, a very high pressure will be obtained during such a filling process, and at the same time a much broader pressure will be obtained than with today's methods. This will mean that a far more compact filling is obtained than is the case today.

The filling material is applied in layers, usually 3–4 layers per cavity, and curing with the aid of light is carried out on each layer whilst the compactor 6 is held in place.

The transparent compactor 6 according to the invention can be attached to a standard amalgam plugger 8.

When the compactor 6 is to be used in the case of, e.g., a one-sided Class II cavity 3, the working part of a standard instrument 8, e.g., a small amalgam plugger, is inserted into the opening 7 in the compactor 6. This opening 7 in the compactor 6 is narrow, so that the working part provides attachment to the compactor 6. The working part has in the end thereof a cylinder and has the effect of allowing the compactor to be turned 360°. This means that only one type—although of different sizes—is required to place fillings on both sides of a tooth. A small amalgam plugger is used as an alternative here, but other instruments which are cylindrical may be as suitable.

The compactor can be made in two-four different sizes so that it is adapted to the most common sizes of Class II cavities. The compactor must be of maximum transparency so as to allow the curing light source to let optimum light pass through the compactor. In addition, the compactor has the suitable shape as described above. The shape means that the compactor releases the filling material easily after use, and does not become stuck in the hole. During use, a maximum pressure down on the tooth and in towards the adjacent tooth is obtained. It is also important that the compactor is made of a plastic material which is soft and flexible and which has optimal "release-capacity", i.e., it releases the filling material easily. A major problem is that today's methods and instruments for placing such fillings result in pull-out of the filling material when the instrument is withdrawn from the fillings. Thus, air bubbles may occur under the material and form weak points between the filling material and tooth, and caries may form here and so cause the whole filling to become loose after a short time.

With the aid of the compactor 6, the filling material 5 will fill even small microdetails, cracks and fissures. This reduces the chance of secondary caries developing which may cause the fillings to become loose and require replacement.

The compactor according to the invention will ensure that there is a considerably greater pressure on a larger surface both down against the tooth and towards the sides of the tooth. The shape of the compactor is optimally adapted to the shape of the tooth, and is produced in a transparent and flexible material which means that the compactor releases easily, so avoiding pull-out of the composite out when the compactor is withdrawn.

This product advantage will mean a far more compact filling which thus will mean a filling of longer life. This in turn will result in fewer dissatisfied patients complaining to their dentist. Dentists will have a greater control of their production, i.e., a greater possibility for quality assurance of their fillings.

What is claimed is:

1. A compactor for placing light-curable filling material (5) in connection with dental treatment, especially for filling a cavity in a tooth which is contiguous with an adjacent tooth, the compactor (6) in the longitudinal direction being conical in shape; an end which is to be pressed down in the filling material has in cross-section a square, rounded shape; the compactor having longitudinal side faces, and one of the longitudinal side faces being concave in form (12), whilst the opposite side face being convex in form (13), and at an opposite end, the compactor is equipped with an opening (11) leading into a hole (7) for connection to a handle.

2. A compactor according to claim 1, wherein it is made of a flexible, elastic and light-penetrable material.

3. A compactor according to claim 1, wherein it is made of plastic.

4. A compactor according to claim 1, wherein it can be connected to a handle, and that it can be rotated 360° relative to the handle.

5. A method for applying a filling material in a dental treatment comprising:

placing a fillable material comprising at least one of a light-curable plastic material or a chemically curable plastic material in a cavity;

compacting the fillable material with a compactor, the compactor:

being conical in shape in the longitudinal direction the compactor having longitudinal side faces one of the longitudinal side faces being concave in form and the opposing side face being convex in form; and having an end which is to be pressed down in the filling having in a cross section a square, rounded shape; and wherein at an end which is furthest from the filling, the compactor includes an opening leading into a hole for connection to a handle.

\* \* \* \* \*